United States Patent
Denissen (10) Patent No.: US 10,820,829 B2
(45) Date of Patent: Nov. 3, 2020

(54) INTERVENTIONAL SYSTEM

(71) Applicant: KONINKLIJKE PHILIPS N.V., Eindhoven (NL)

(72) Inventor: Sander Hans Denissen, Veldhoven (NL)

(73) Assignee: KONINKLIJKE PHILIPS N.V. (NL)

(*) Notice: Subject to any disclaimer, the term of this patent is extended or adjusted under 35 U.S.C. 154(b) by 1468 days.

(21) Appl. No.: 14/761,036

(22) PCT Filed: Jan. 28, 2014

(86) PCT No.: PCT/IB2014/058601
§ 371 (c)(1),
(2) Date: Jul. 15, 2015

(87) PCT Pub. No.: WO2014/125388
PCT Pub. Date: Aug. 21, 2014

(65) Prior Publication Data
US 2016/0015293 A1     Jan. 21, 2016

Related U.S. Application Data

(60) Provisional application No. 61/764,594, filed on Feb. 14, 2013.

(51) Int. Cl.
*A61B 5/05* (2006.01)
*A61B 5/06* (2006.01)
(Continued)

(52) U.S. Cl.
CPC .............. *A61B 5/063* (2013.01); *A61B 5/044* (2013.01); *A61B 5/0422* (2013.01); *A61B 5/065* (2013.01);
(Continued)

(58) Field of Classification Search
None
See application file for complete search history.

(56) References Cited

U.S. PATENT DOCUMENTS

| 7,772,541 | B2 | 8/2010 | Froggatt et al. |
| 8,185,192 | B2 | 5/2012 | Markowitz et al. |
| (Continued) | | | |

FOREIGN PATENT DOCUMENTS

| JP | 2009539566 A | 11/2009 |
| WO | 2011048509 A1 | 4/2011 |

*Primary Examiner* — Joel F Brutus (57) ABSTRACT

The invention relates to an interventional system comprising an interventional device (11) for being inserted into a living being (7) and comprising an optical shape sensing fiber, wherein the optical shape sensing fiber is used for determining respiratory motion by monitoring a movement of a part of the interventional device, which moves in accordance with the respiratory motion. Thus, respiratory motion can be determined, without necessarily requiring a physician to handle with further devices like a respiratory belt, i.e. the same interventional device can be used for performing an interventional procedure and for determining the respiratory motion. The interventional procedure can therefore be less cumbersome for a physician. Moreover, since the determination of the respiratory motion is based on optical shape sensing, which is a very accurate position determination technique, the respiratory motion can be determined very accurately.

14 Claims, 3 Drawing Sheets

(51) Int. Cl.
    *A61B 5/042*    (2006.01)
    *A61B 5/00*     (2006.01)
    *A61B 5/113*    (2006.01)
    *A61B 5/044*    (2006.01)
    *A61B 5/11*     (2006.01)
    *A61B 34/20*    (2016.01)

(52) U.S. Cl.
    CPC ............ *A61B 5/1102* (2013.01); *A61B 5/113* (2013.01); *A61B 5/6858* (2013.01); *A61B 5/721* (2013.01); *A61B 5/7246* (2013.01); *A61B 2034/2061* (2016.02); *A61B 2562/0233* (2013.01)

(56) References Cited

U.S. PATENT DOCUMENTS

| | | |
|---|---|---|
| 8,773,650 B2 | 7/2014 | Froggatt et al. |
| 9,138,165 B2 | 9/2015 | Holsing et al. |
| 9,784,569 B2 | 10/2017 | Froggatt et al. |
| 2004/0097806 A1* | 5/2004 | Hunter ............... A61B 1/00071 600/434 |
| 2009/0137952 A1* | 5/2009 | Ramamurthy ........... A61B 5/06 604/95.01 |
| 2010/0030063 A1 | 2/2010 | Lee et al. |
| 2011/0282187 A1 | 11/2011 | Harley et al. |
| 2012/0197097 A1* | 8/2012 | Chan ................. A61B 1/00165 600/342 |
| 2012/0289777 A1 | 11/2012 | Chopra et al. |
| 2013/0150732 A1 | 6/2013 | Manzke et al. |
| 2013/0211261 A1 | 8/2013 | Wang et al. |
| 2013/0223702 A1 | 8/2013 | Holsing et al. |
| 2014/0148677 A1 | 5/2014 | Liempde et al. |

\* cited by examiner

INTERVENTIONAL SYSTEM

CROSS-REFERENCE TO PRIOR APPLICATIONS

This application is the U.S. National. Phase application under 35 U.S.C. § 371 of International Application Serial No. PCT/IB2014/058601, filed on Jan. 28, 2014, which claims the benefit of U.S. Application Ser. No. 61/764,594, filed on Feb. 14, 2013. These applications are hereby incorporated by reference herein.

FIELD OF THE INVENTION

The invention relates to an interventional system, an interventional method and an interventional computer program.

BACKGROUND OF THE INVENTION

In interventional procedures respiratory motion is often a problem. For instance, in procedures for generating an electroanatomical map of a heart of a person it is generally difficult to assign a measured electrical cardiac signal to a correct anatomical position, because of the movement of the heart induced by breathing. Or, as a further example, in ablation procedures, during which the heart should be ablated at a certain anatomical position, it is difficult to assure that really the desired anatomical position is ablated due to the motion of the heart caused by breathing. In order to overcome this respiratory motion problem, technically relatively complex techniques for capturing the respiratory motion are known like using a respiratory belt, tracking positions of markers attached to the breast of the person by using tracking devices like cameras, et cetera. However, these techniques for detecting respiratory motion are cumbersome for a physician and not very accurate.

SUMMARY OF THE INVENTION

It is an object of the present invention to provide an interventional system, an interventional method and an interventional computer program, which allow for an accurate and less cumbersome detection of respiratory motion during an interventional procedure.

In a first aspect of the present invention an interventional system is presented, wherein the interventional system comprises:

an interventional device for being inserted into a living being, wherein the interventional device comprises an optical shape sensing fiber, a position determination unit for determining positions of a part of the interventional device, which moves in accordance with respiratory motion of the living being, by using the optical shape sensing fiber, a respiratory motion determination unit for determining the respiratory motion of the living being depending on the determined positions of the part of the interventional device.

Since the position determination unit determines positions of a part of the interventional device, which moves in accordance with respiratory motion of the living being, by using the optical shape sensing fiber, the respiratory motion can be determined depending on these determined positions of the part of the interventional device, without necessarily requiring a physician to handle with further devices like a respiratory belt, markers on the breast and additional tracking devices for tracking the motion of the markers, et cetera.

The respiratory motion can be determined by just using an optical shape sensing signal provided by the optical shape sensing fiber, which is present in the interventional device, such that the determination of the respiratory motion during an interventional procedure is less cumbersome for a user. Moreover, since the determination of the respiratory motion is based on optical shape sensing, which is a very accurate position determination technique, the respiratory motion can be determined very accurately.

The interventional device is preferentially an elongated device like a catheter having a functional distal tip. The distal tip may be adapted for energy application purposes like ablation purposes, sensing purposes like sensing tissue properties within the living being, et cetera. The optical shape sensing fiber is preferentially arranged along the entire elongated interventional device, i.e. from its proximal end to the distal tip, and the position determination unit is preferentially also adapted to determine the position of the distal tip of the elongated interventional device by using the optical shape sensing fiber, i.e. the same optical shape sensing fiber can be used for determining the position of the tip of the elongated device and for determining the respiratory motion. Thus, also for determining the position of the tip of the elongated interventional device an additional tracking system is not necessarily required, thereby further simplifying the use of the interventional system by a physician.

The part of the interventional device, which moves in accordance with respiratory motion of the living being, preferentially rests against a part of the living being, which moves substantially only due to breathing, in order to very accurately determine the respiratory motion. For instance, if the distal tip of the interventional device has been inserted into the heart of a person, the part of the interventional device, which is used for determining the respiratory motion, preferentially rests against an inner wall of the living being at a position between the abdominal aorta and the aortic arch.

The respiratory motion determination unit is preferentially adapted to determine the respiratory cycles and the respiratory phases of the respiratory cycles as a respiratory motion based on the determined positions of the part of the interventional device, which moves in accordance with the respiratory motion.

It is preferred that the interventional system further comprises:

an electrical field generating device for generating an electrical field within the living being, wherein the interventional device comprises a sensing part with a sensing element for sensing the electrical field, wherein the position determination unit is adapted to determine the position of the sensing element at different locations within the living being by using the optical shape sensing fiber, an electrical signal measuring unit for measuring electrical signals being indicative of the electrical field at the determined positions of the sensing part by using the electrical field generating device and/or the sensing element, and a correlation map determination unit for determining a correlation map defining a correlation between positions and electrical signals based on the determined positions of the sensing element and the measured electrical signals.

Since the correlation map is determined based on positions of the sensing element, which have been determined by using an optical shape sensing technique, the correlation map is very accurate. The correlation map can be used by another interventional device, which does not need to comprise an optical shape sensing fiber, but which is equipped with a sensing element like an electrode, for determining the position of this further interventional device within the living being. In particular, the electrical signal measuring unit can be adapted to measure an electrical signal by using the electrical field generating device and/or the sensing element of the further interventional device and this measured electrical signal can be used together with the correlation map for determining the actual position of the further interventional device within the living being.

The sensing part can comprise one or several sensing elements. The one or several sensing elements are preferentially electrodes, which have been inserted into the living being, and the electrical field generating device preferentially comprises electrodes and a voltage source for generating the electrical field, wherein the electrodes of the electrical field generating device can be attached to an outside surface of the living being like the breast or they can be attached to an inner surface of the living being like an inner surface of the heart.

The electrical signal measuring unit can be adapted to measure the electrical signal by performing the measurement directly at the sensing element or by measuring a change in the electrical field generating device caused by inductions in the sensing element.

It is further preferred that the correlation map determination unit is adapted to determine a respiratory compensated correlation map based on the determined positions of the sensing element, the measured signals and the determined respiratory motion. In particular, the respiratory motion determination unit is preferentially adapted to determine the respiratory phase as the respiratory motion depending on the determined position of the part of the interventional device, which moves in accordance with the respiratory motion, wherein the sensing part is a distal part of the interventional device to be used in a heart of the living being, wherein the interventional system further comprises a respiratory phase assignment providing unit for providing assignments between positions of the heart and the respiratory phase, wherein the correlation map determination unit is adapted to determine the respiratory compensated correlation map based on the determined positions of the sensing element, the measured signals, the determined respiratory phases and the provided assignments. This leads to a more accurate correlation map.

It is further preferred that the interventional system comprises a cardiac motion determination unit for determining cardiac motion, wherein the correlation map determination unit is adapted to determine a cardiac compensated correlation map based on the determined positions of the sensing element, the measured signals and determined cardiac motion. Preferentially, the correlation map determination unit is adapted to compensate for cardiac motion and for respiratory motion. The correlation map determination unit can further be adapted to compensate for a movement of the living being not being respiratory or cardiac motion. This leads to an even further improved correlation map.

The interventional device preferentially comprises a distal portion, a proximal portion and an intermediate portion, wherein the sensing part is located in the distal portion. It is further preferred that the position determination unit is adapted to determine the position of a part of the intermediate portion, which moves in accordance with the respiratory motion of the living being, by using the optical shape sensing fiber.

It is also preferred that the interventional device is adapted to be inserted into a heart of the living being and comprises a sensing part with a sensing element for sensing electrical cardiac signals at a heart wall at different locations, wherein the position determination unit is adapted to determine the position of the sensing element at the different locations by using the optical shape sensing fiber, wherein the interventional system further comprises a) an electrical cardiac signal measuring unit for measuring the electrical cardiac signals at the heart wall at the different locations by using the sensing element, b) an anatomical map providing unit for providing an anatomical map of the heart, and c) an electroanatomical map determination unit for determining an electroanatomical map defining a correlation between anatomical positions and electrical cardiac signals based on the determined positions of the sensing element, the measured electrical cardiac signals and the provided anatomical map. Since the electroanatomical map is determined based on positions, which have been determined by using optical shape sensing fiber technology, the electroanatomical map is very accurate. Preferentially, the interventional system is adapted to determine both, a correlation map and an electroanatomical map, by using the same interventional device, i.e. by using the same optical shape sensing fiber and the same sensing part with the one or several sensing elements. This allows for a fast and accurate determination of the correlation map and the electroanatomical map by using a single device, which makes the handling of the interventional system for determining the correlation map and the electroanatomical map relatively simple.

The electroanatomical map determination unit is preferentially adapted to determine a respiratory compensated electroanatomical map based on the determined positions of the sensing element, the measured electrical cardiac signals, the provided anatomical map and the determined respiratory motion. In particular, the respiratory motion determination unit is preferentially adapted to determine the respiratory phase as the respiratory motion depending on the determined position of the part of the interventional device, which moves in accordance with the respiratory motion, wherein the sensing part is a distal part of the interventional device to be used in a heart of the living being, wherein the interventional system further comprises a respiratory phase assignment providing unit for providing assignments between positions of the heart and the respiratory phase, wherein the electroanatomical map determination unit is adapted to determine the respiratory compensated electroanatomical map based on the determined positions of the sensing element, the measured electrical cardiac signals, the determined respiratory phases and the provided assignments. This leads to a further improved electroanatomical map.

The interventional system may further comprise a cardiac motion determination unit for determining cardiac motion, wherein the electroanatomical map determination unit is adapted to determine a cardiac compensated electroanatomical map based on the determined positions of the sensing part, the measured electrical cardiac signals, the provided anatomical map and determined cardiac motion. Preferentially, the electroanatomical map determination unit is adapted to compensate for cardiac motion and for respiratory motion. The electroanatomical map determination unit can further be adapted to compensate for a movement of the living being not being respiratory or cardiac motion. This leads to an even further improved electroanatomical map.

In a preferred embodiment the interventional device comprises a sensing part having a basket structure with several elongated elements, along which several sensing elements are arranged, wherein at least one of the elongated elements comprises an optical shape sensing fiber, wherein the position determination unit is adapted to determine the shape, orientation and position of the elongated element comprising the optical shape sensing fiber by using the optical shape sensing fiber and to determine the positions of the sensing elements based on the shape, orientation and position of the elongated element comprising the optical shape sensing fiber and predefined spatial relationships between the elongated element comprising the optical shape sensing fiber and the sensing elements. Thus, a single optical shape sensing fiber may be used for determining very accurately the positions of several sensing elements arranged along the several elongated elements. The interventional device can therefore be very compact and relatively small, because it is not necessarily required to use several optical shape sensing fibers for determining the positions of the several sensing elements.

In an embodiment the position determination unit is adapted to determine the position of a part of the interventional device, which moves in accordance with cardiac motion of the living being, by using the optical shape sensing fiber, wherein the interventional system further comprises a cardiac motion determination unit for determining the cardiac motion of the living being depending on the determined position of the part of the interventional device. Thus, also the cardiac motion may be determined without requiring additional cardiac motion tracking means. In particular, the same optical shape sensing fiber may be used for determining the position of, for instance, the distal tip of the interventional device, for determining the respiratory motion and for determining the cardiac motion, wherein different parts of the same optical shape sensing fiber are used for determining the position of the distal tip and the different motions. A further part of the same optical shape sensing fiber may be used for determining a movement of the living being, especially a patient movement, which is not a cardiac movement or a respiratory movement, by using a further part of the same optical shape sensing fiber, which does not move in accordance with cardiac motion and respiratory motion. Thus, different kinds of motion may be determined by just using the interventional device having the optical shape sensing fiber, which makes these determinations relatively easy for a physician.

In a further aspect of the present invention an interventional method is presented, wherein the interventional method comprises:

determining positions of a part of an interventional device comprising an optical shape sensing fiber by using the position determination unit, while the part moves in accordance with respiratory motion of a living being, by using the optical shape sensing fiber, and determining the respiratory motion of the living being depending on the determined positions of the part of the interventional device by a respiratory motion determination unit.

In a further aspect of the present invention a computer program is presented, wherein the computer program comprises program code means for causing an interventional system, to carry out the steps of the interventional method, when the computer program is run on a computer controlling the interventional system.

It shall be understood that the interventional system, the interventional method, and the computer program have similar and/or identical preferred embodiments, in particular, as defined in the dependent claims.

It shall be understood that a preferred embodiment of the invention can also be any combination of the dependent claims or above embodiments with the respective independent claim.

These and other aspects of the invention will be apparent from and elucidated with reference to the embodiments described hereinafter.

DETAILED DESCRIPTION OF EMBODIMENTS

Figure 1:
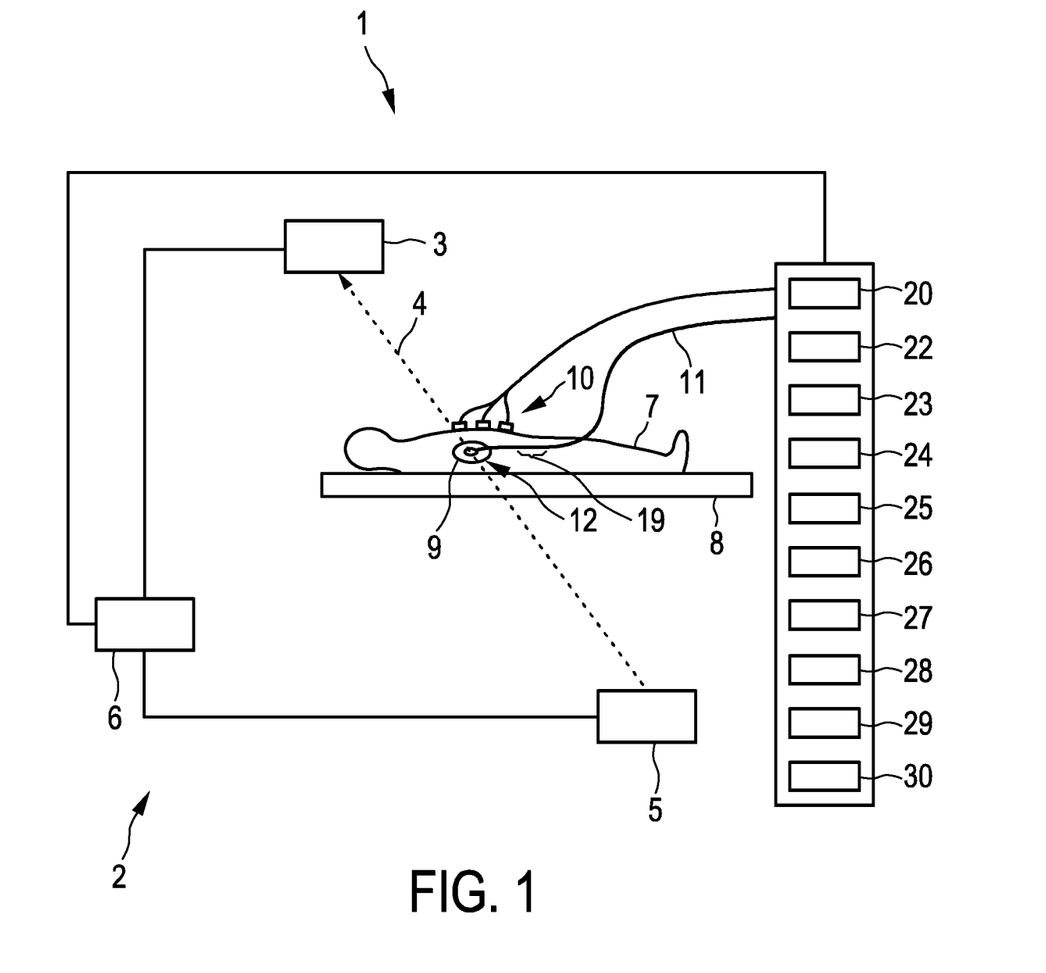
FIG. 1 shows schematically and exemplarily an embodiment of an interventional system.

FIG. 1 shows schematically and exemplarily an interventional system 1 comprising an interventional device 11 for being inserted into a person 7, wherein the interventional device 11 comprises an optical shape sensing fiber. The interventional system 1 further comprises a position determination unit 20 for determining positions of a part 19 of the interventional device 11, which moves in accordance with respiratory motion of the person 7, by using the optical shape sensing fiber, and a respiratory motion determination unit 22 for determining the respiratory motion of the person 7 depending on the determined positions of the part 19 of the interventional device 11. The person 7 is located on a support means like a patient table 8.

Figure 2:
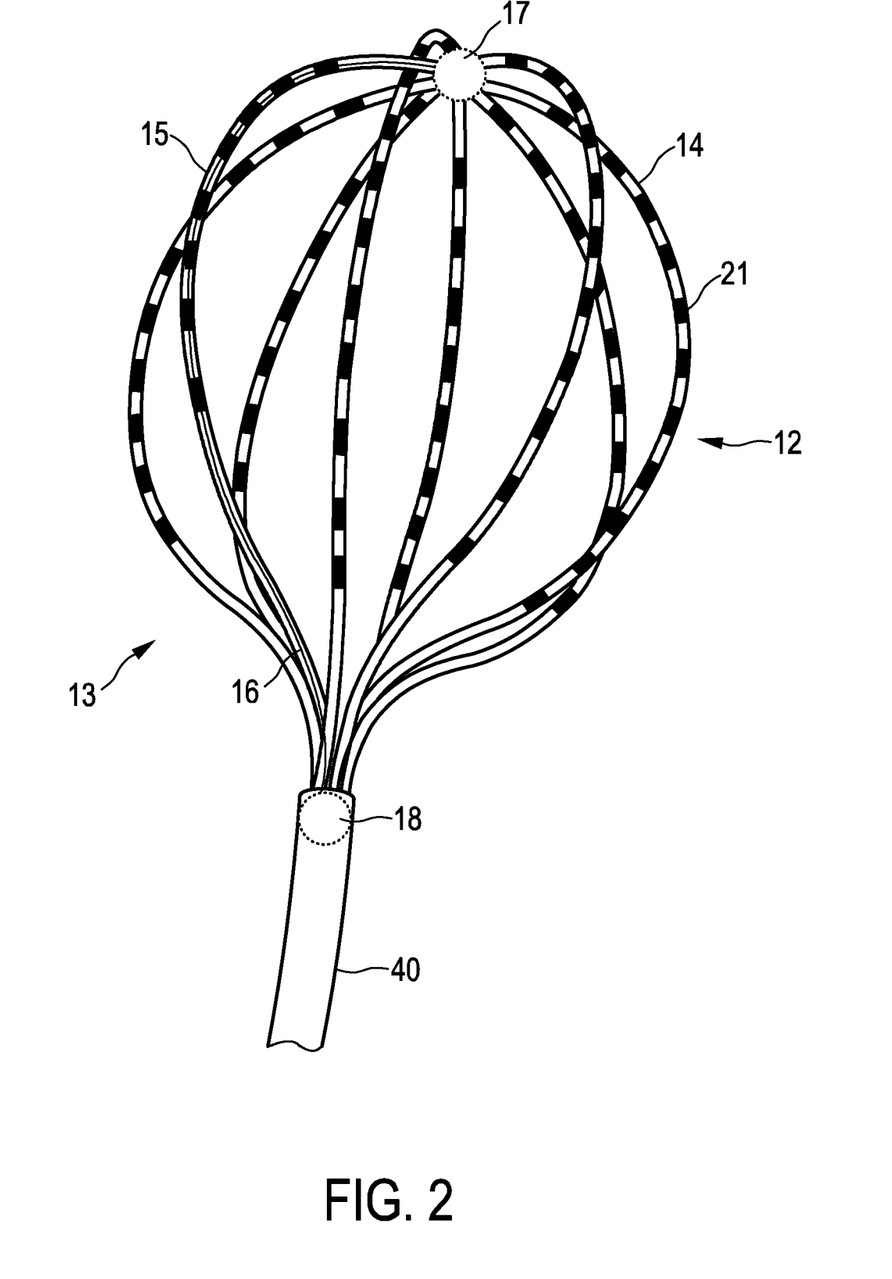
FIG. 2 shows schematically and exemplarily an embodiment of a tip of an interventional device of the interventional system.

In this embodiment the interventional device is a catheter 11 having a functional distal tip 12, which is schematically and exemplarily shown in more detail in FIG. 2 and which is adapted for sensing electrical signals, wherein the optical shape sensing fiber 16 extends along the entire catheter 11, i.e. from the functional tip 12 to the position determination unit 20. The position determination unit 20 can therefore determine the position of each part of the catheter 11, for instance, also of the distal functional tip 12 of the catheter 11, by using the optical shape sensing fiber 16. The position determination unit 20 can be adapted to use known optical shape sensing techniques for determining the position of a certain part of the catheter 11. For instance, the technique disclosed in U.S. Pat. No. 7,772,541 B2 or the technique disclosed in EP 2 478 331 A2 can be used for determining the position of a certain part of the catheter 11.

The part 19 of the catheter 11 rests against a part of the person 7, which moves substantially only due to breathing, in order to very accurately determine the respiratory motion. In this embodiment, the distal functional tip 12 is adapted to sense electrical signals in the heart 9 of the person 7. Thus, if the tip 12 of the catheter 11 has been inserted into the heart 9 of the person 7, the position determination unit 20 preferentially determines positions of a part 19 of the catheter 11, which rests against an inner wall of the person 7 at a location between the abdominal aorta and the aortic arch.

The respiratory motion determination unit 22 is adapted to determine the respiratory cycles and the respiratory phases of the respiratory cycles as the respiratory motion based on the determined positions of the part 19, which moves in accordance with the respiratory motion. For instance, a respiratory cycle can be determined as the time needed by the part 19 to reach a same position again, wherein this time can be divided into different temporal sections for defining the respiratory phases of the respiratory cycle.

Thus, the respiratory motion can be determined by finding a repeating movement of a middle section, i.e. an intermediate part, of the optical shape sensing fiber. The exact portion of the optical shape sensing fiber may be determined by using anatomical mapping, which can be determined by x-ray registration using an x-ray projection system 2, which will be described in more detail further below. In particular, x-ray projection images generated by the x-ray projection system 2 can be used for registering different portions of the optical shape sensing fiber with different anatomical positions of parts of the person 7, wherein this x-ray registration can be used for determining the part 19 of the catheter 11, i.e. the respective portion of the optical shape sensing fiber, which moves in accordance with the respiratory motion. The part 19 of the catheter 11, which moves in accordance with the respiratory motion, can also be determined in another way, for instance, by using a computed tomography system for registering the anatomical positions within the person 7 with different parts of the catheter 11. Also certain bendings of the catheter 11, which are present, when the distal tip of the catheter 11 has been inserted into the heart 9 of the person 7, can be used for determining the part 19 of the catheter 11, which moves in accordance with the respiratory motion. For instance, the actual bends of the catheter 11 can be compared with expected bends for identifying an iliac bend and the large bend of the aortic arch, wherein a part between these bends can be determined as being the part 19 of the catheter 11, which moves in accordance with the respiratory motion.

For determining the phases of the respiratory cycle the knowledge may be used that the respiratory cycle generally has a certain time span and follows a specific motion pattern, if coughs are excluded. For instance, motion periods corresponding to predefined possible ranges of time spans and/or predefined motion patterns can be identified as the respiratory cycles and these respiratory cycles can be subdivided into the different respiratory phases. The determined respective respiratory phase can be stored as a floating point value or as a percentage of the respective entire cycle and can be correlated to a rigid transformation of the heart 9. In particular, a movement of the heart 9 caused by breathing can be measured by using, for instance, the x-ray projection system 2 during a respiratory cycle, wherein to each phase of the respiratory cycle a respective position of the heart 9 can be assigned for determining the rigid transformation of the heart.

The distal functional tip 12 of the catheter 11 forms a sensing part 13 of the catheter 11. The sensing part 13 has a basket structure with several elongated elements 14, 15, along which several sensing elements 21 are arranged. In this embodiment, the sensing elements 21 are electrodes and the elongated elements 14, 15 comprise a memory shape material like Nitinol, which is shaped such that, if the elongated elements 14, 15 are not forced into a tubular casing 40 of the catheter 11, a basket structure is formed. In other embodiments other materials and constructions can be used for providing a deployable basket structure. One elongated element 15 comprises the optical shape sensing fiber 16, wherein the position determination unit 20 is adapted to determine the shape, orientation and position of the elongated element 15 comprising the optical shape sensing fiber 16 by using the optical shape sensing fiber 16 and to determine the positions of the sensing elements 21 based on the shape, orientation and position of the elongated element 15 comprising the optical shape sensing fiber 16 and predefined spatial relationships between the elongated element 15 comprising the optical shape sensing fiber 16 and the sensing elements. The predefined spatial relationships can be direct relationships, which provide direct assignments between the shape, orientation and position of the elongated element 15 and, thus, of the optical shape sensing fiber 16 and positions of the sensing elements, or indirect relationships, which describe how the positions of the sensing elements depend on the shape, orientation and shape of the elongated element 15 and, thus, of the optical shape sensing fiber 16 and which may be defined as rules or a sequence of position determination steps, which can be used to determine the positions of the sensing elements by directly or indirectly using the shape, orientation and shape of the elongated element 15, i.e. of the optical shape sensing fiber 16.

For instance, the position determination unit 20 can be adapted to determine the distance between the first point 17 and the second point 18 shown in FIG. 2 for determining the degree of deployment of the basket structure. The position determination unit 20 can also be adapted to determine the degree of deployment in another way. For example, for each location along the optical shape sensing fiber 16 between the two points 17, 18 a vector from the respective location to the center axis of the basket structure can be determined, wherein these vectors can be used by the position determination unit 20 for determining the degree of deployment of the basket structure. Moreover, the position determination unit 20 can determine a twist value, which can be used to determine the orientation of the basket structure. Since also the position of the basket structure is known by the position determination unit 20 by using the optical shape sensing fiber 16, the determined degree of deployment, orientation and position of the basket structure can be used together with predefined known positions of the sensing elements 21 with respect to the basket structure for determining the positions of the sensing elements 21 with respect to a reference system defined by the optical shape sensing detection technique. It should be noted that in FIG. 2 the points 17, 18 are shown for explanatory purposes only and are of course not part of the real basket structure.

Especially if the sensing part of the catheter has another structure, the positions of the sensing elements can also be determined in another way. Generally, the positions of the sensing elements along the sensing part of the catheter, i.e. the positions of the sensing elements with respect to the sensing part of the catheter, are known, for instance, at the device manufacture time. The position, shape and orientation of the optical shape sensing fiber with respect to the sensing part of the catheter are also known such that also the positions of the sensing elements with respect to the position, shape and orientation of the optical shape sensing fiber are known. Thus, by determining the position, shape and orientation of the optical shape sensing fiber in three dimensions also the positions of the sensing elements with respect to the reference system defined by the optical shape sensing technique can be determined in three dimensions.

The interventional system 1 further comprises an electrical field generating device 10 for generating an electrical field within the heart 9 and an electrical signal measuring unit 24 for measuring electrical signals being indicative of the electrical field at the positions of the sensing elements 21 by using the electrical field generating device 10 and/or the sensing elements 21. The electrical field generating device 10 comprises several electrodes like electrocardiography leads, which are connected to a voltage source 23 for providing the electrical field within the heart 9. In this embodiment the electrodes of the electrical field generating device 10 are attached to the breast of the person 7. However, in other embodiments the electrodes of the electrical field generating device 10 can also be attached to another outer surface of the person 7. Moreover, the electrodes of the electrical field generating device 10 could also be attached to an inner surface of the person 7.

The electrical signal measuring unit 24 can be adapted to measure the electrical signals by performing the measurement directly at the sensing elements 21, i.e. electrical signals measured by the sensing elements 21 can be used as the electrical signals provided by the electrical signal measuring unit 24, or the electrical signal measuring unit 24 can be adapted to measure a change in the electrical field generating device 10 caused by inductions in the sensing elements 21 and to provide this change as the electrical signals.

The interventional system 1 further comprises a correlation map determination 25 for determining a correlation map defining a correlation between positions and electrical signals based on positions of the sensing elements 21, which have been determined by the position determination unit 20, and electrical signals measured at these positions by using the electrical signal measuring unit 24. In particular, the correlation map determination unit 25 is adapted to determine a respiratory compensated correlation map based on the determined positions of the sensing elements 21, the measured signals and the determined respiratory motion. For instance, a respiratory phase assignment providing unit 26 can provide predefined assignments between positions of the heart 9 and the respective respiratory phase, wherein the correlation map determination unit 25 can be adapted to determine the respiratory compensated correlation map based on the determined positions of the sensing elements 21, the signals measured by the electrical signal measuring unit 24, the determined respiratory phases and the provided assignments. Thus, the respiratory cycle, particularly the respiratory phases, can be used to determine the displacement of the heart with respect to the patient anatomy caused by breathing, wherein this determined displacement can be used for determining the respiratory compensated correlation map. The respiratory phase assignment providing unit 26 can also be adapted to provide assignments between positions of the heart and positions of the electrodes of the electric field generating device 10, in order to allow the correlation map determination 25 to determine displacements of these electrodes on the person 7 caused by breathing, which can be used for determining a correlation map having an improved respiratory compensation.

The interventional system 1 further comprises a cardiac motion determination unit 27 for determining cardiac motion, wherein the correlation map determination unit 25 is adapted to determine also a cardiac compensated correlation map based on the determined positions of the sensing elements 21, the signals measured by the electrical signal measuring unit 24 and the determined cardiac motion. Thus, the correlation map determination unit 25 can be adapted to determine a correlation map, which is not only compensated with respect to respiratory motion, but also with respect to cardiac motion. Also the cardiac motion is preferentially determined as cycles and phases, i.e. as cardiac cycles and cardiac phases. For instance, positions of a part of the catheter 11, which moves in accordance with substantially only cardiac motion, can be determined and used for determining the cardiac cycles and cardiac phases. However, also other measurements can be used for determining the cardiac cycles and cardiac phases. For instance, the electrodes of the electrical field generating device 10 can be adapted to measure an electrocardiogram, which can be used by the cardiac motion determination unit 27 for determining the cardiac cycles and cardiac phases.

If positions of a part of the catheter 11, which moves in accordance with substantially only cardiac motion, are used for determining the cardiac cycles and cardiac phases, this part is preferentially a repeatedly moving near-distal portion of the catheter 11. The knowledge that the heart cycle is of a certain time span and follows a specific motion pattern can be used for determining the respective cardiac phase in the cardiac cycle. For instance, motion periods corresponding to predefined possible ranges of time spans and predefined motion patterns can be identified as the cardiac cycles and these cardiac cycles can be subdivided into the different cardiac phases. The respective cardiac phase may be stored as a floating point value or as a percentage of the respective entire cardiac cycle.

The optical shape sensing fiber 16 is preferentially used for determining the position of the distal tip 12 of the catheter 11 and for determining the respiratory motion. As described above, the same optical shape sensing fiber can also be used for determining cardiac motion. Moreover, the same optical shape sensing fiber, i.e. a further part of the same optical shape sensing fiber, may be used for determining a movement of the person 7, which is not a cardiac movement or a respiratory movement, by using a further part of the same optical shape sensing fiber 16, which does not move in accordance with cardiac motion and respiratory motion. Also this person movement, which is not a cardiac movement or a respiratory movement, can be used by the correlation map determination unit 25, in order to provide a correlation map, which is also compensated for this kind of motion. Thus, different kinds of motion can be determined by just using the interventional device 11 having the optical shape sensing fiber 16, which may be used by the correlation map determination unit 25 for determining a correlation map, which is compensated for these different kinds of motion.

In particular, the positions of the electrodes can be corrected for respiratory motion of the heart 9 by using the determined correlation between the respiratory phases and the respective positions of the heart 9, i.e. since for each respiratory phase the displacement of the heart 9 caused by respiratory motion is known, this displacement can be used for determining the three-dimensional position of the respective electrode at the respective respiratory phase with respect to the anatomy of the heart 9. In order to compensate for cardiac motion, a minimal motion cardiac phase may be selected and electrical signals and corresponding three-dimensional positions of the electrodes with respect to the anatomy of the heart may be determined only for these minimal motion cardiac phases. Alternatively, the three-dimensional positions may be stored together with the respective cardiac phase and a four-dimensional model of the heart may be used for determining for each cardiac phase the respective three-dimensional position of the respective electrode with respect to the anatomy of the heart. For a possible further compensation of the three-dimensional position of the respective electrode with respect to motion of the person 7 relative to the support means 8, which is not caused by cardiac motion or respiratory motion, a displacement of the person 7 with respect to the support means 8 can be determined by using the optical shape sensing fiber and this displacement can directly be used for determining the position of the respective electrode with respect to the anatomy of the heart. After the compensated three-dimensional position of the respective electrode within the heart 9 has been determined, the respective measured electrical signal can be mapped to this respective electrode position.

This mapping of electrical signals to three-dimensional positions may be performed as described in US 2011/0282187 A1.

The measured electrical signals may be affected by impedance effects and changes in the positions of the electrodes of the electrical field generating device due to the respiratory motion. This effect on the measured electrical signals can be determined by acquiring the electrical signals, while the sensing part is held statically. Changes in the electrical signals measured by the sensing part of the catheter while it is held statically are indicative of this effect such that these changes can be used for correcting this effect. For instance, an additional rigid transformation can be used or this effect can be subtracted as a base signal from the measured electrical signals.

The correlation map can be used by another interventional device, which does not need to comprise an optical shape sensing fiber, but which has to be equipped with a sensing element like an electrode, for determining the position of this further interventional device within the person 7. In particular, the electrical signal measuring unit 24 can be adapted to measure an electrical signal by using the electrical field generating device 10 and/or the sensing element of the further interventional device and this measured electrical signal can be used together with the correlation map for determining the actual position of the further interventional device within the person 7. An electrode based tracking can therefore be provided.

For instance, when inducing an electrical current in the sensing elements 21 of the basket structure, the measured signal in an electrocardiogram, which may be acquired by the electrodes of the electrical field generating device 10, changes in a repeatable manner, when the positions of the sensing elements 21 of the basket structure change with respect to the positions of the electrodes of the electrical field generating device 10. Since these measured signals are correlated with the positions of the sensing elements 21 of the basket structure, which have been determined very accurately by using the optical shape sensing fiber, a very accurate correlation map can be determined. The correlation map can then be used together with an actually measured change in the signal provided by the electrodes of the electrical field generating device 10, when a further interventional device having an electrode moves within the heart 9, for determining the position of the electrode of this further interventional device. For determining the positions of the electrodes depending on the correlation map triangulation may be used, for example, as disclosed in US 2011/0282187 A1.

The interventional system 1 further comprises an electrical cardiac signal measuring unit 28 for measuring electrical cardiac signals at an inner wall of the heart 9 at different locations within the heart 9 by using the sensing elements 21. The interventional system 1 also comprises an anatomical map providing unit 29 for providing an anatomical map of the heart 9 and an electroanatomical map determination unit 30 for determining an electroanatomical map defining a correlation between an anatomical position and electrical cardiac signals based on positions of the different locations of the sensing elements 21, at which the electrical cardiac signals have been measured, the measured electrical cardiac signals and the provided anatomical map. The positions of the locations, at which the sensing elements 21 have measured the electrical cardiac signals, are determined by the position determination unit 20 by using the optical shape sensing fiber 16. The anatomical map is preferentially a three-dimensional anatomical map of the heart 9 of the person 7, which may have been determined based on a three-dimensional image of the heart 9 of the person 7, which has been acquired before the interventional procedure. The three-dimensional image is, for instance, a computed tomography image or a magnetic resonance image, which may have been segmented for generating the three-dimensional anatomical map of the heart 9. For registering the provided anatomical map of the heart 9 with the reference system defined by the optical shape sensing technique, the x-ray projection system 2 may be used.

The x-ray projection system 2 comprises an x-ray source 5 for providing x-ray radiation 4 for traversing the heart 9 and an x-ray detector 3 for detecting the x-ray radiation 4, after having traversed the heart 9. The x-ray projection system 2 may further comprise an x-ray control unit 6 for controlling the x-ray projection system 2 and for generating x-ray projection images depending on the x-ray radiation detected by the x-ray detector 3. The x-ray projection system 2 can be an x-ray C-arm system for generating x-ray projection images in different directions. The x-ray projection images generated by the x-ray projection system 2 preferentially show the catheter 11, in particular, the distal part 12 of the catheter 11, and the anatomy of the heart 9 such that the x-ray projection images can be used for registering the provided anatomical map of the heart 9, which also shows the anatomy of the heart 9, with the reference system defined by the optical shape sensing technique. In other embodiments other registration methods can be used for registering the provided anatomical map of the heart 9 with respect to the reference system defined by the optical shape sensing detection.

The electroanatomical map determination unit 30 is preferentially adapted to determine a respiratory compensated electroanatomical map based on the determined positions of the sensing elements 21, the measured electrical cardiac signals, the provided anatomical map and the determined respiratory motion. In particular, the electroanatomical map determination unit 30 is preferentially adapted to determine the respiratory compensated electroanatomical map based on the determined positions of the sensing elements 21, the measured electrical cardiac signals, the determined respiratory phases and the assignments between positions of the heart and the respiratory phases provided by the respiratory phase assignment providing unit 26. For instance, these assignments can provide displacements of the heart with respect to the anatomy of the person 7 depending on the respiratory phases, wherein these displacements can be used for determining a respiratory motion compensated electroanatomical map.

The electroanatomical map determination unit 30 can further be adapted to use the cardiac motion determined by the cardiac motion determination unit 27, in particular, the determined cardiac phases, for determining a cardiac motion compensated electroanatomical map based on the determined positions of the sensing elements 21, the electrical cardiac signals measured at these positions, the provided and registered anatomical map and the determined cardiac phases. The electroanatomical map determination unit 30 can also be adapted to compensate for a further movement of the person 7 not being respiratory or cardiac motion.

For determining a cardiac motion compensated electroanatomical map the cardiac phase can be determined, which corresponds to minimal cardiac motion, wherein the electroanatomical map determination unit 30 can be adapted to determine the electroanatomical map for this determined cardiac phase that corresponds to minimal cardiac motion. Selecting the minimal cardiac motion phase as the acquisition phase to map the electrical signals to the positions of the electrodes in three dimensions allows determining an electroanatomical map being substantially static with respect to the cardiac motion. Moreover, since for each measured electrical signal the respective respiratory phase has been determined, the corresponding three-dimensional position of the respective electrode can be compensated for respiratory motion of the heart 9 by using the determined correlation between respiratory phases and positions of the heart 9, in order to correct the determined three-dimensional positions of the electrodes by undoing the heart movement due to respiratory motion such that the respective three-dimensional position is known with respect to the anatomy of the heart 9. This allows the electroanatomical map determination unit 30 to indicate the respective electrical signal at the three-dimensional anatomical position of the heart by, for instance, labeling the respective signal strength using a color to either generate a voxel of said color in three dimensions or tag a voxel or a mesh triangle on the three-dimensional anatomical map of the heart, which may also be regarded as being a three-dimensional model of the heart, with this color.

The different positions of the heart for different respiratory phases have been determined for a certain position of the person 7 on the support means 8. In order to consider a possible movement of the person 7 with respect to the support means 8, the determined further movement of the person 7 not being respiratory or cardiac motion can be used. In particular, if the person 7 has moved along a certain distance with respect to the support means 8, this certain distance can be considered, while determining the three-dimensional position of the respective electrode with respect to the anatomy of the heart 9.

Figure 3:
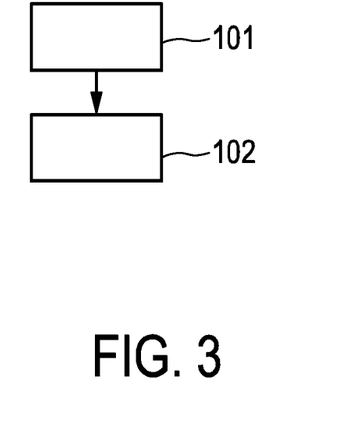
FIG. 3 shows a flowchart exemplarily illustrating an embodiment of an interventional method.

In the following an embodiment of an interventional method will exemplarily be described with reference to a flowchart shown in FIG. 3.

In step 101 positions of a part of the interventional device 11 comprising the optical shape sensing fiber 16 are determined by the position determination unit 20, while the part moves in accordance with respiratory motion of the person 7, by using the optical shape sensing fiber 16. In step 102 the respiratory motion determination unit 22 determines the respiratory motion of the person 7 depending on the determined positions of the part of the interventional device 11. The interventional method can optionally comprise further steps like the measurement of electrical signals and the determination of a correlation map and/or an electroanatomical map as described above, wherein the respiratory motion can be used for determining a respiratory compensated correlation map and/or electroanatomical map. The interventional method can also comprise further steps like the determination of further kinds of motion, in particular, of cardiac motion and/or motion of the person, which is not respiratory motion and not cardiac motion, wherein these additional kinds of motion can be used for determining a correlation map and/or an electroanatomical map, which is also compensated for these kinds of motion.

Optical shape sensing is a technology that uses reflections inside preferentially four cores of a multi-core optical fiber to measure local strain on each individual core. The strain on each core is caused by tension caused by bends. These bends can be calculated back from the strain information and with that the entire shape. The fiber is small enough to fit into most medical devices that are introduced, for instance, endovascularly or endoluminally.

The use of the optical shape sensing fiber during the generation of the three-dimensional electroanatomical map, which may be an electrophysiological map, of the heart can increase the speed and level of accuracy of generating the electroanatomical map.

The optical shape sensing fiber and the position determination unit can be adapted to determine positions along the optical shape sensing fiber at distances being 50 µm or smaller. The position of the optical shape sensing fiber and, thus, the positions of the electrodes along the arm, i.e. along the elongated element, of the basket structure, which comprises the optical shape sensing fiber, are known from the optical shape sensing. The positions of the electrodes on the other arms are preferentially at a known distance along the respective other arm. When the basket is deployed, the deployment can be measured using the shape sensed coordinates and thereby the location of the electrodes on the other arms with respect to the coordinate system of the fiber shape detection can be determined. This coordinate system is at a known transformation from the x-ray coordinate system, i.e. the coordinate system of the x-ray projection system, by performing a rigid registration before or during the interventional procedure.

The basket structure is preferentially inserted into the heart of the person in a non-deployed condition, in which the arms are substantially parallel. After the tip of the interventional device, i.e. the basket structure, has been inserted into the heart, it is deployed, for instance, as shown in FIG. 2, in order to start, for example, the mapping procedure for determining the electroanatomical map. During the mapping procedure a proximal section, i.e. a section being proximal with respect to the distal tip, of the shape sensing fiber may be used to track patient movement and breathing motion. The breathing motion may be used to keep track of the position of the heart with respect to the external frame of reference, which may be defined by the coordinate system of the fiber shape detection. The patient motion can be used to track the position of the patient with respect to the external frame of reference; for example to overlay a pre-operative computed tomography image of the patient onto the determined three-dimensional electroanatomical map.

The cardiac phase may be extracted from shape data provided by the optical shape sensing fiber or by other cardiac data like data received from an electrocardiograph, in particular, from the electrical field generation device. To provide context for the user, the electroanatomical map may be overlaid with a multi-phase pre- or intraoperative three-dimensional computed tomography or cone beam computed tomography image, wherein the cardiac phase may be used to select the three-dimensional image computed tomography image or cone beam computed tomography image having the correct phase.

Inducing current into the electrodes of the basket structure will show a change in signal in multiple channels of the electrocardiogram, i.e. changes in signals obtained from the electrodes of the electrical field generating device, and will affect the signals in different ways depending on the location of the electrodes of the basket structure. These changes in the signals depending on the locations of the electrodes of the basket structure can be used for creating the correspondence map, i.e. the correlation map, as described above.

The positions of the part of the optical shape sensing fiber, which moves in accordance with the cardiac motion, can be used for determining the moment of minimal movement, wherein the interventional system can be adapted to determine the electroanatomical map for this moment only. For determining this minimal movement moment also an electrocardiogram signal can be used.

Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality.

A single unit or device may fulfill the functions of several items recited in the claims. The mere fact that certain measures are recited in mutually different dependent claims does not indicate that a combination of these measures cannot be used to advantage.

Determinations like the determination of positions of the sensing elements based on optical shape sensing signals, determinations of respiratory motion, cardiac motion or other kinds of motion, determinations of correlation maps and electroanatomical maps, et cetera performed by one or several units or devices can be performed by any other number of units or devices. For example, the position determination unit and the respiratory motion determination unit can be a single unit or any other number of different units. The determinations and/or the control of the interventional system in accordance with the interventional method can be implemented as program code means of a computer program and/or as dedicated hardware.

A computer program may be stored/distributed on a suitable medium, such as an optical storage medium or a solid-state medium, supplied together with or as part of other hardware, but may also be distributed in other forms, such as via the Internet or other wired or wireless telecommunication systems.

Any reference signs in the claims should not be construed as limiting the scope.

The invention relates to an interventional system comprising an interventional device for being inserted into a living being and comprising an optical shape sensing fiber, wherein the optical shape sensing fiber is used for determining respiratory motion by monitoring a movement of a part of the interventional device, which moves in accordance with the respiratory motion. Thus, respiratory motion can be determined, without necessarily requiring a physician to handle with further devices like a respiratory belt, i.e. the same interventional device can be used for performing an interventional procedure and for determining the respiratory motion. The interventional procedure can therefore be less cumbersome for a physician. Moreover, since the determination of the respiratory motion is based on optical shape sensing, which is a very accurate position determination technique, the respiratory motion can be determined very accurately.

The invention claimed is:

1. An interventional system comprising:
an interventional device comprising an optical shape sensing fiber, and including a distal portion to be inserted into a heart of a living being for performing ablation and/or sensing a property within the living being, a proximal portion, and an intermediate portion adapted to move in accordance with respiratory motion of the living being;
a position determination unit for determining positions of the distal portion and a part of the intermediate portion of the interventional device over time using the optical shape sensing fiber; and
a respiratory motion determination unit for determining the respiratory motion of the living being depending on the determined positions of the part of the intermediate portion of the interventional device, while the distal portion is inserted in the heart, to compensate for the respiratory motion when performing the ablation and/or sensing the property within the living being.

2. The interventional system as defined in claim 1, further comprising:
an electrical field generating device for generating an electrical field within the living being, wherein the interventional device further comprises a sensing part with a sensing element for sensing the electrical field, wherein the position determination unit is adapted to determine positions of the sensing element at different locations within the living being using the optical shape sensing fiber;
an electrical signal measuring unit for measuring electrical signals being indicative of the electrical field at the determined positions of the sensing part by using the electrical field generating device and/or the sensing element; and
a correlation map determination unit for determining a correlation map defining a correlation between positions and electrical signals based on the determined positions of the sensing element and the measured electrical signals.

3. The interventional system as defined in claim 2, wherein the correlation map determination unit is adapted to determine a respiratory compensated correlation map based on the determined positions of the sensing element, the measured signals and the determined respiratory motion.

4. The interventional system as defined in claim 3, wherein the respiratory motion determination unit is adapted to determine a respiratory phase as the respiratory motion depending on the determined position of the part of the intermediate portion of the interventional device, which moves in accordance with the respiratory motion, wherein the sensing part is at the distal portion of the interventional device to be used in the heart of the living being, wherein the interventional system further comprises a respiratory phase assignment providing unit for providing assignments between positions of the heart and the respiratory phase, and wherein the correlation map determination unit is adapted to determine the respiratory compensated correlation map based on the determined positions of the sensing element, the measured signals, the determined respiratory phases and the provided assignments.

5. The interventional system as defined in claim 2, further comprising a cardiac motion determination unit for determining cardiac motion, wherein the correlation map determination unit is adapted to determine a cardiac compensated correlation map based on the determined positions of the sensing element, the measured signals and determined cardiac motion.

6. The interventional system as defined in claim 1, wherein a sensing part of the interventional device is located in the distal portion.

7. The interventional system as defined in claim 1, wherein the interventional device further comprises a sensing part with a sensing element for sensing electrical cardiac signals at a heart wall at different locations, wherein the position determination unit is adapted to determine positions of the sensing element at the different locations using the optical shape sensing fiber, wherein the interventional system further comprises:
an electrical cardiac signal measuring unit for measuring the electrical cardiac signals at the heart wall at the different locations by using the sensing element;
an anatomical map providing unit for providing an anatomical map of the heart; and an electroanatomical map determination unit for determining an electroanatomical map defining a correlation between anatomical positions and electrical cardiac signals based on the determined positions of the sensing element, the measured electrical cardiac signals and the provided anatomical map.

8. The interventional system as defined in claim 7, wherein the electroanatomical map determination unit is adapted to determine a respiratory compensated electroanatomical map based on the determined positions of the sensing element, the measured electrical cardiac signals, the provided anatomical map and the determined respiratory motion.

9. The interventional system as defined in claim 7, wherein the respiratory motion determination unit is adapted to determine a respiratory phase as the respiratory motion depending on the determined position of the part of the intermediate portion of the interventional device, which moves in accordance with the respiratory motion, wherein the interventional system further comprises a respiratory phase assignment providing unit for providing assignments between positions of the heart and the respiratory phase, wherein the electroanatomical map determination unit is adapted to determine a respiratory compensated electroanatomical map based on the determined positions of the sensing element, the measured electrical cardiac signals, the determined respiratory phases and the provided assignments.

10. The interventional system as defined in claim 7, wherein the interventional system further comprises a cardiac motion determination unit for determining cardiac motion, wherein the electroanatomical map determination unit is adapted to determine a cardiac compensated electroanatomical map based on the determined positions of the sensing part, the measured electrical cardiac signals, the provided anatomical map and determined cardiac motion.

11. The interventional system as defined in claim 1, wherein the interventional device further comprises a sensing part having a basket structure with elongated elements, along which sensing elements are arranged, wherein at least one of the elongated elements comprises the optical shape sensing fiber, wherein the position determination unit is adapted to determine the shape, orientation and position of the at least one elongated element by using the optical shape sensing fiber and to determine the positions of the sensing elements based on the shape, orientation and position of the elongated element comprising the optical shape sensing fiber and predefined spatial relationships between the at least one elongated element comprising the optical shape sensing fiber and the sensing elements.

12. The interventional system as defined in claim 1, wherein the position determination unit is adapted to determine a position of the part of the interventional device, which moves in accordance with cardiac motion of the living being, by using the optical shape sensing fiber, wherein the interventional system further comprises a cardiac motion determination unit for determining the cardiac motion of the living being depending on the determined position of the part of the interventional device.

13. A computer program element comprising instructions to control an interventional system comprising an interventional device comprising an optical shape sensing fiber, and including a distal portion to be inserted into a heart of a living being for performing ablation and/or sensing a property within the living being, and an intermediate portion adapted to move in accordance with respiratory motion of the living being, the instructions, when being executed by a processing unit, cause the interventional system to carry out steps of an interventional method, comprising:
 determining positions of the distal portion and a part of the intermediate portion of the interventional device over time, using the optical shape sensing fiber, and
 determining the respiratory motion of the living being depending on the determined positions of the part of the intermediate portion of the interventional device, while the distal portion is inserted in the heart;
 compensating for the respiratory motion when performing the ablation and/or sensing the property within the living being.

14. A non-transitory computer readable medium having stored thereon the computer program element of claim 13.

* * * * *